United States Patent [19]

Gordon

[11] Patent Number: 4,590,922

[45] Date of Patent: May 27, 1986

[54] USE OF FERROMAGNETIC, PARAMAGNETIC AND DIAMAGNETIC PARTICLES IN THE TREATMENT OF INFECTIOUS DISEASES

[76] Inventor: Robert T. Gordon, 4936 W. Estes, Skokie, Ill. 60077

[21] Appl. No.: 524,844

[22] Filed: Aug. 19, 1983

[51] Int. Cl.$^4$ ............................................. A61B 19/00
[52] U.S. Cl. ........................................ 128/1.3; 128/1.1
[58] Field of Search ................... 128/1.1, 1.3, 1.5, 399, 128/804; 422/20, 21, 22

[56] References Cited

U.S. PATENT DOCUMENTS

| | | | |
|---|---|---|---|
| 2,407,690 | 9/1946 | Southworth | 128/422 |
| 3,474,777 | 10/1969 | Figge et al. | 128/1.3 |
| 4,106,488 | 8/1978 | Gordon | 128/1.1 |
| 4,269,826 | 5/1981 | Zimmermann et al. | 128/1.3 |
| 4,308,229 | 12/1981 | Voit | 422/20 |

FOREIGN PATENT DOCUMENTS 2508802  7/1981  France .................... 128/1.3

*Primary Examiner*—Edward M. Coven
*Attorney, Agent, or Firm*—Scully, Scott, Murphy and Presser

[57] ABSTRACT

This invention provides a method of treatment of infectious disease organisms comprising introducing minute particles into the interior of infectious cells. These particles possess ferromagnetic, paramagnetic or diamagnetic properties. After being localized intracellularly, these particles are inductively heated by application of an alternating electromagnetic field. The inductive heating is continued for a period of time sufficient to bring about an intracellular temperature rise to a minimum necessary to kill the infectious organism.

26 Claims, No Drawings

USE OF FERROMAGNETIC, PARAMAGNETIC AND DIAMAGNETIC PARTICLES IN THE TREATMENT OF INFECTIOUS DISEASES

BACKGROUND OF THE INVENTION

At present, one of the major methods of treatment of infectious disease is the administration of chemotherapeutic agents, either synthetic (e.g., sulfonilamides) or natural (e.g. streptomycin). Generally speaking, the methods produce the desired affect of inhibition or destruction of the infectious agent by interfering with one or more of its metabolic pathways in some manner. Although certainly effective, the use of these substances may have a number of undesirable side effects. For example, many patients may experience sensitive or allergic reactions, kidney and gastrointestinal tract irritation, or nerve damage. This is in large part due to the homology between the metabolic pathways of the host and the invading organism. This is especially a problem in the case where both pathogen and host are eukaryote, such as in fungal diseases of man. Further, the use of antibiotics may promote development of resistant forms of the pathogens, a problem with serious long-term side effects extending beyond just the individual patient.

Alternatively, with a disease in which the metabolic pathways of the causative agent are unknown or poorly understood, oftentimes the symptoms alone are treated until the natural immunity of host can respond. In such a case the obvious danger is that considerable, possibly irreversible, damage may be done by the pathogen before the host's defenses have had sufficient time to combat the infection.

A method of treatment of infectious organisms which avoids these difficulties is clearly desirable. To be completely successful, the treatment should kill the invading organism while causing substantially no harm to the host's tissues. Also, the treatment should be such that there is little or no chance for the organisms being treated to become tolerant or resistant to the treatment method. Also desirable would be a method of treatment, which would permit the destruction of an organism about which only a minimum of information is known concerning its metabolic pathways. One potential method is to focus upon a particular aspect of the infectious organism's metabolism which differs from that of the host cells, and, rather than interfering with the pathways as antibiotics do, to exploit the organism's routine use of that pathway in such a way that it may be turned against the organism, eventually killing it.

An example of such a potentially useful pathway is that by which infectious organisms acquire and store iron. For convenience, the invention will be described in relation to iron metabolism, but as will be made clear below, the invention is not limited to embodiments relating to iron metabolism per se.

Numerous investigations have been conducted to determine the method of uptake of iron by microorganisms from their environment. It has been found that many groups of microbes differ in their mode of iron acquisition, and most appear to differ fundamentally in the pathways employed by the cells of higher organisms. For example, it is widely accepted that bacteria may produce chelating agents which have high affinity for certain metals, and particularly ferric iron. In all studied enteric bacteria, such as Salmonella, Enterobacter, Klebsiella, and Escherichia, this chelator is enterochelin, a cyclic trimer of 2,3-dihydroxybenzoylserine (Rosenberg and Young, Microb. Iron Metab., J. B. Nielands, ed., p. 67, 1974). The mycobacteria produce a series of secondary hydroxamates known as mycobactins, and also salicylic acid. Bacillus (sps) are known to utilize 2,3-dihydroxybenzoylglycine for iron transport (Byers, Microb. Iron Metab., J. B. Nielands, ed., p. 83, 1974). In most cases, these substances are excreted into the environment where they bind iron, and the entire iron-chelator complex is reabsorbed by the bacterium.

Iron transport mechanisms have been characterized in microorganisms other than bacteria as well. *Ustilago sphaerogena*, a smut fungus, utilizes the cyclic hexapeptide desferri-ferrichrome as its iron carrier (Emery, Microb. Iron Metab., J. B. Nielands, ed., p. 107, 1974). In protozoa, ingestion of ferric hydroxide particles by pinocytosis is probably the mechanism of iron uptake. Certain RNA viruses have also been shown to bind terbium to their nucleic acid (Morley, et al., Biochem. Biophys. Res. Comm., 101:1123, 1981).

It is also known that a wide variety of metal-containing molecules occur naturally with the microbial cell; the most familiar of these are the porphyrins, and especially important among these are the protoporphyrins, including the chlorophylls and cytochromes. However, many microorganisms are also known to contain specific iron-sulfur containing proteins, such as ferredoxin and rubredoxin, which serve as electron-transfer factors (Lovenberg, Microb. Iron Metab., J. B. Nielands, ed., p. 161, 1974). These proteins may be of different structures in the various organisms from which they have been isolated, but always consist of an iron-containing center which may consist of from one iron (rubredoxin) up to four irons (Clostridium ferredoxin).

Minute particles possessing ferromagnetic, paramagnetic or diamagnetic properties have been shown to be particularly useful in treating cancer, as described by R. T. Gordon in U.S. Pat. No. 4,106,488 and U.S. patent application Ser. No. 464,870, filed Feb. 8, 1983, incorporated herein by reference. As exemplified therein, ferric hydroxide and gallium citrate are used to form particles of a size 1 micron or less, and are introduced into the cancer cells in the area to be treated. The cells of the chosen area are then subjected to a high frequency alternating magnetic field, inductively heating the intracellular particles, resulting in an increase in intracellular temperature. Because the cancer cells accumulate the particles to a greater degree than normal cells, and because they also have a higher resting temperature than normal cells, the increase in temperature kills the cancer cells and leaves the normal cells substantially unharmed. The present invention is predicated on the discovery that with certain modification, the intracellular hyperthermia technique as disclosed by Gordon may be effectively utilized in destroying the cells of infectious organisms, exploiting the specificity of some of their metabolic pathways and metal-containing, metabolizable products to selectively concentrate the magnetic particles within the cells of the disease-causing organisms, or to selectively focus the inductive heating process upon magnetic particles found naturally only in the infectious cells.

BRIEF DESCRIPTION OF THE INVENTION

This invention relates to a method of treatment of infectious disease organisms comprising providing said organisms with minute, inductively heatable, intracellularly localizable particles of a size less than 1 micron and inductively heating said particles by the application of an alternating electromagnetic field for a period of time sufficient to effect a rise in intracellular temperature to a minimum necessary to kill the infectious organism.

The particles best suited for this treatment are pharmacologically acceptable ferromagnetic, paramagnetic or diamagnetic particles. These possess magnetic properties uniquely suited for treatment and diagnostic regimens as disclosed in applicant's U.S. Pat. Nos. 4,106,488; 4,136,683 and 4,303,636.

Said particles may be selected from the group comprising ferromagnetic, paramagnetic or diamagnetic inorganic elements and compounds as well as organic compounds such as metal dextran complexes, metal-containing prosthetic groups, transport or storage proteins and the like. The invention may utilize either particles exogenously supplied to the infectious cells, or such particles endogenous to the infectious cells, in the form of one of the above-mentioned elements or compounds. Infectious organisms for which the treatment proves particularly useful are found among the viruses, bacteria, fungi and protozoa.

DETAILED DESCRIPTION OF THE INVENTION

The present invention achieves a precise increment of heat rise within the cells of the infectious organism. On the basis of the cell resting temperature and the thermal sensitivity of the individual infectious organism, the internal temperature of the invading cell is raised to the minimum necessary to cause cell death. In accordance with the present invention, there are found to be a number of approaches which can achieve the end result of destroying the infectious organism's cells without causing damage to the host's cells.

In its broadest aspect, the invention proposes the introduction into the infectious cells of minute particles of a ferromagnetic, paramagnetic or diamagnetic material. Particularly useful particles include both inorganic elements and compounds as well as metal containing organic compounds. Inorganic elements and compounds particularly well-suited, owing to their favorable magnetic parameters, comprise elements such as dysprosium, erbium, europium, gallium, holmium, samarium, terbium, thulium, ytterbium or yttrium and compounds thereof, such as dysprosium sulfate, erbium sulfate, europium oxide, europium sulfate, holmium oxide, samarium sulfate, terbium oxide, terbium sulfate, thulium oxide, ytterbium sulfide, yttrium oxide, yttrium sulfate, yttrium ferrioxide ($Y_3Fe_5O_{12}$) and yttrium aluminum oxide ($Y_3Al_5O_{12}$).

Metal containing organic molecules useful for the application discussed above comprise particles of iron-dextrans such as FeOOH-dextran complexes and other dextran complexes and other dextran metal complexes wherein the metal is selected from the group comprising cobalt, zinc, chromium, nickel, platinum, manganese and rare earth metals such as dysprosium, erbium, europium, gallium, holmium, samarium, terbium, thulium, ytterbium and yttrium, ferric ammonium citrate, enterochelin, hydroxamates, phenolates, ferrichromes, ferritin, ferric mycobactins, and iron-sulfur proteins such as ferredoxin and rubredoxin.

Particularly appropriate metal containing organic structures for use with the present invention are the porphyrins such etioporphyrins, mesoporphyrins, uroporphyrins, coproporphyrins, protoporphyrins, and dicarboxylic acid containing porphyrins and substituted porphyrins such as tetraphenylporphyrin sulfonate (TTPS). Especially advantageous protoporphyrins comprise hematoporphyrins, chlorophylls, and cytochromes. In addition to the naturally occurring protoporphyrins which possess iron or magnesium containing moieties, mixed metal hybrid porphyrins may also be prepared. For example, by substituting an alternative metal for the iron in hematoporphyrin, the advantages of the porphyrin moiety (e.g., in terms of specificity of localization) is retained while the unique magnetic properties of the new metal enhance the sensitivity of the substituted molecule. Suitable metals for purposes of substitution comprise cobalt, manganese, zinc, chromium, nickel, platinum and rare earth series of metals dysprosium, erbium, europium, gallium, holmium, samarium, terbium, thulium, ytterbium and ytterium. Suitable porphyrin acceptors comprise any dicarboxylic acid containing porphyrin, such as protoporphyrins (e.g., hematoporphyrins) and the like.

The principle upon which the present invention is based is grounded in the discovery that infectious organisms may transport, metabolize and sequester many elements or compounds in quite a different manner from that of the cells of the more advanced host organisms it usually infects. In one aspect of this invention, this specificity is used to selectively concentrate the above-mentioned minute particles within the cells of the infectious organisms, with little or no uptake of said particles by the host cells.

The particles introduced into the infectious cells will generally be infectious organism-specific, i.e., an element or compound peculiar to the metabolism of the organism being treated. Compounds which are particularly useful in this regard are any of the above-mentioned metal-chelating transport substances specific to the various groups of microorganisms. Also potentially of value in this process are such metal-containing organic structures as the porphyrins, including hematoporphyrins, cytochromes and chlorophylls. In addition to the naturally occurring porphyrins, mixed metal hybrid porphyrins may be prepared, substituting manganese, zinc, cobalt, chromium, nickel, platinum and rare earth series of metals such as dysprosium, erbium, europium, gallium, holmium, samarium, terbium, thulium, ytterbium and yttrium.

The minute particles described are to be administered to the patient either orally or parenterally, i.e., intravenously, intramuscularly, intraperitoneally, subcutaneously, topically or in suppository form, depending upon the nature and localization of the infection. Dosage and frequency of administration may also vary depending upon the nature of the infectious organism.

The next stage of the present invention is to differentially kill the infectious cells by causing inductive heating within the cytoplasm of said cells using a high-frequency alternating electromagnetic field, bringing about a precise rise in temperature of the cell. The principle of inductive heating through the use of hysteresis is a known principle. Similarly, the monitoring of the temperatures of the living cells is a presently available technique well known to medical science.

Inductive heating of the minute particles is achieved through use of an electric oscillator operating in the high frequency range which heats the particles by subjecting them to an intense high-frequency field within a large but otherwise conventional helical coil, field energy being converted to heat through hysteresis losses and the resistor dissipation of eddy currents. The helical induction coil is of sufficient internal diameter to permit the patient to pass within and of such length to encompass the length of the patient. Preferably the internal diameter would be greater than 3-6 feet in diameter, since diameters of inductive coils of greater than 6 feet have a preferential effect on the overall process by providing a minor uniform flux gradient to the patient.

The frequency of the electromagnetic alternating high-frequency field will range from 1 kilohertz to 100 megahertz, and the power input of the oscillator-generator will range from 0 kilowatts to 30 kilowatts per Kg. of patient body weight 1 kilowatts of power per 1.0 kilograms of body weight. In this power and frequency range, the colis selected to produce from 0 to $5 \times 10^4$ oersteds, preferably from 10 to 10,000 oersteds.

The time necessary to inductively heat the minute particles held within the infectious cells depends substantially upon the frequency and the power production of the alternating electromagnetic field and ultimately the strength of the field produced. It should be noted, however, that it is only necessary to raise the temperature of the infectious cell to the minimum required to cause cell death, concentration of particles in the vehicles and the and that the variables with respect to the type and electromagnetic treatment are not critical provided that the necessary temperature is attained.

In a further embodiment of the invention, treatment may be accomplished by inductive heating of magnetic particles endogenous to the invading cells. As noted above, many types of microorganisms possess metal-containing compounds routinely in the cell; among these are storage proteins or metabolically essential porphyrins such a hematoporphyrin, chlorophylls, or cytochromes. For example, a large number of organisms produce ferredoxins or rubredoxins, iron-sulfur storage proteins which differ from genus to genus in their structure and the amount of bound iron. These are not found in the cells of most higher organisms. Also other compounds, such as certain cytochromes or ferritin, while they may also occur in host cells, have been shown to generally be different in structure from those of the host organism. The difference in structure between microbial metal-containing compounds and host cell metal-containing compounds implies a difference in magnetic characteristics, such as magnetic susceptibility, between the pathogen's compounds and those of the host cells. Magnetic susceptibility is known to be temperature dependent, and may be routinely measured by magnetometer devices. By measuring the magnetic susceptibilities of particles at certain temperatures, it is possible to calibrate the magnetometer equipment so that measurement of magnetic susceptibility indicates the exact temperature of the particle in question. This capability may be used to selectively monitor the internal temperature of the invading cell (as described by Gordon in U.S. Pat. No. 4,106,488, and copending U.S. patent application Ser. No. 464,870 for the treatment of cancer cells) by focusing on the magnetic susceptibility of a particle unique to the pathogen, and bringing about a precise rise in temperature sufficient to kill the pathogenic cells without harming the host cells.

As noted above, there are a number of naturally occurring compounds which would be eminently suitable for employing this method of treatment. A partial list of compounds specific to a particular organism or organisms, which have magnetic characteristics that may prove particularly useful in this regard, is represented in the following table:

|  | Compound |
|---|---|
| Fungi |  |
| Phycomyces[1] | Ferritin |
| Saccharomyces[2] | Yeast cytochrome a |
| Candida[2] |  |
| Bacteria |  |
| E. coli[3] | Bacterio-ferritin |
| Clostridium[4] | clostridial ferredoxin |
| Pseudomonas[4] | pseudomonad ferredoxin |
|  | putidaredoxin |
| Peptostreptococcus[4] | rubredoxin |
| Numerous protozoan[2] and bacterial species | cytochrome o |

[1](David, C., Microb. Iron Metab., J.B. Nielands, ed., p. 149, 1974).
[2](Yamanaka, T. and Okunuki, K., Microb. Iron Metab., J.B. Nielands, ed., p. 349, 1974).
[3](Rosenberg, H. and Young, J.G., Microb. Iron Metab., J.B. Nielands, ed., p. 67, 1974).
[4](Lovenberg, W., Microb. Iron Metab., J.B. Nielands, ed., p. 349, 1974).

This list is intended only to be exemplary, and is not limiting as to possible other applications of the treatment. The above-described treatment method is particularly well-suited to the treatment of organisms for which the metabolic pathways are poorly known, and for which there is no known chemotherapeutic agent. All that would be necessary is the identification of a specific metal-containing compound endogenous to the infectious organism, and said treatment would then be applicable.

A further embodiment of the invention is the surface sterilization of objects using ferromagnetic, paramagnetic or diamagnetic particles. In this application of the invention, unsterile objects may be immersed in a solution containing said particles, which may be in the form of any of the compounds or elements mentioned in the previous embodiments. The concentration of the particles in solution would not be critical. The contaminating organisms would, over a period of time, take up the particles and concentrate them within their cytoplasm. A high-frequency alternating magnetic field could then be applied to the objects raising the internal temperature of the contaminating organism by inductive heating, and eventually killing them. Because of the nature of this application of the invention, precise control of the temperature rise below a certain level would not be necessary, since no host cells are involved. This method provides a unique way of ridding objects, such as surgical instruments, of potentially dangerous microorganisms.

What is claimed is:

1. A method of treatment of infectious disease organisms comprising:
   providing to said organism minute, inductively heatable, intracellularly-localizable particles of a size less than 1 micron, and
   inductively heating said particles by the application of an alternating electromagnetic field for a period of time sufficient to effect a rise in intracellular temperature to a minimum necessary to kill said organism.

2. The method according to claim 1 wherein said infectious organisms are selected from the group comprising viruses, bacteria, fungi and protozoa.

3. The method according to claim 2 wherein said infectious organisms comprise Salmonella, Klebsiella, Escherichia, Clostridium, Mycobacterium, Pseudomonas, Peptostreptococcus, Phycomyces, Candida, Ustilago, Entamoeba, Trypanosoma, Leishmania and RNA viruses.

4. The method according to claim 1 wherein said particles are selected from the group comprising ferromagnetic, paramagnetic and diamagnetic elements, inorganic compounds, organic compounds and combinations thereof.

5. The method according to claim 4 wherein said particles are selected from the group comprising
   (a) inorganic metals and compounds comprising dysprosium, erbium, europium, gallium, holmium, samarium, terbium, thulium, ytterbium, or yttrium, dysprosium sulfate, erbium sulfate, europium oxide, europium sulfate, holmium oxide, samarium sulfate, terbium sulfate, thulium oxide, ytterbium sulfide, yttrium oxide, yttrium sulfate, yttrium ferrioxide ($Y_3Fe_5O_{12}$) and yttrium aluminum oxide ($Y_3Al_5O_{12}$);
   (b) metal containing organic compounds comprising dextran metal complexes wherein said metal is selected from the group comprising cobalt, zinc, chromium, nickel, platinum, manganese and rare earth metals dysprosium, erbium, gallium, holmium, samarium, terbium, thulium, ytterbium, yttrium and iron;
   (c) iron transport and chelating compounds comprising ferric ammonium citrate, enterochelin, hydroxamates, phenolates, ferrichromes, desferri-ferrichromes, ferritin, ferric mycobactins and iron sulfur proteins; and
   (d) porphyrins comprising etioporphyrins, mesoporphyrins, uroporphyrins, coproporphyrins, protoporphyrins and dicarboxylic acid containing porphyrins such as tetraphenylporphyrin sulfonate, hematoporphyrins, chlorophylls and cytochromes.

6. The method according to claim 5 wherein said iron dextran complexes comprise FeOOH-dextran complexes.

7. The method according to claim 5 wherein said iron-sulfur proteins comprise ferredoxin and rubredoxin.

8. The method according to claim 5 wherein said dicarboxylic acid porphyrins comprise tetraphenylporphyrin sulfonate, hematoporphyrins, chlorophylls and cytochromes.

9. A method of treatment of infectious disease organisms within a living host without substantially damaging normal host cells comprising:
   introducing into the host minute, intracellularly-localizable particles capable of being inductively heated and of a size less than 1 micron whereby said minute particles are selectively absorbed into the infectious cells; and
   inductively heating said particles by exposing the host to an alternating electromagnetic field for a period of time sufficient to attain a rise in intracellular temperature to a minimum necessary to kill the infectious cells.

10. The method according to claim 9 wherein said particles may be administered either orally or parenterally.

11. The method according to claim 10 wherein said parenteral administration comprises introduction of particles intravenously, intramuscularly, intraperitoneally, topically, or in suppository form.

12. The method according to claim 9 wherein infectious organisms are selected from the group comprising viruses bacteria, fungi and protozoa.

13. The method according to claim 12 wherein said infectious organisms are selected from the group comprising Salmonella, Klebsiella, Escherichia, Clostridium, Mycobacterium, Pseudomonas, Peptostreptococcus, Phycomyces, Candida, Ustilago, Entamoeba, Trypanosoma, Leishmania and RNA viruses.

14. The method according to claim 9 wherein said particles are selected from the group comprising ferromagnetic, paramagnetic, or diamagnetic elements, inorganic compounds, organic compounds and combinations thereof.

15. The method according to claim 9 wherein particles are selected from the group comprising:
   (a) ferric hydroxide, and iron dextrans,
   (b) iron and iron chelating compounds comprising ferric ammonium citrate, enterochelin, hydroxamates, phenolates, desferri-ferrichromes, ferritin, ferric mycobactins, and iron sulfur proteins,
   (c) protoporphyrin containing molecules.

16. The method according to claim 15 wherein said iron sulfur proteins comprise ferredoxin and rubredoxin.

17. The method according to claim 15 wherein said protoporphyrin containing molecules comprise cytochromes.

18. A method of treatment of infectious disease organisms within a living host without substantially damaging normal host cells comprising:
   introducing into the host infectious organism-specific, intracellularly localizable particles capable of being inductively heated and of a size less than 1 micron;
   selectively concentrating said particles within the infectious organism; and
   differentially killing the infectious organism by exposing the host to an alternating electromagnetic field, thereby inductively heating said particles for a period of time sufficient to attain a rise in intracellular temperature to a minimum necessary to kill the infectious cells.

19. A method of treatment of infectious disease organisms without substantially damaging normal cells comprising:
   inductively heating particles endogenous to said organism by application of an alternating electromagnetic field for a period of time sufficient to bring about a rise in intracellular temperature to a minimum necessary to kill the infectious organism.

20. The method according to claim 19 wherein said organisms are selected from the group comprising viruses, bacteria, fungi and protozoa.

21. The method according to 20 wherein said organisms are selected from the group comprising Salmonella, Klebsiella, Escherichia, Clostridium, Mycobacterium, Pseudomonas, Peptostreptococcus, Phycomyces, Candida, Ustilago, Entamoeba, Trypanosoma, Leishmania and RNA viruses.

22. The method according to claim 20 wherein said particles are selected from the group comprising ferromagnetic, paramagnetic or diamagnetic elements, inorganic compounds, organic compounds or combinations thereof.

23. The method according to claim 20 in which said particles are selected from the group comprising ferritins, ferrodoxins, rubredoxins and cytochromes.

24. A method of surface sterilization of inanimate objects having contaminating organisms comprising:
   placing said object in a particle containing solution, allowing sufficient time for absorption of said particles by contaminating organisms, inductively heating said particles by application to the object of an alternating electromagnetic field for a period of time sufficient to attain a rise in intracellular temperature to a level necessary to kill the contaminating organisms.

25. The method according to claim 24 wherein said particles are selected from the group comprising ferromagnetic, paramagnetic and diamagnetic elements, inorganic compounds, organic compounds and combinations thereof.

26. The method according to claim 24 wherein said contaminating organism is selected from the group comprising viruses, bacteria, fungi and protozoa.

* * * * *

UNITED STATES PATENT OFFICE
CERTIFICATE OF CORRECTION

Patent No. 4,590,922     Dated May 27, 1986

Inventor(s) Robert T. Gordon

It is certified that error appears in the above-identified patent and that said Letters Patent are hereby corrected as shown below:

Column 5, line 23 delete "concentration of particles in the vehicles and the and that the variables with respect to the type and electromagnetic treatment are not critical provided that the necessary temperature is attained.

INSERT: --and that the variables with respect to the type and concentration of particles in vehicles and the electromagnetic treatment are not critical provided that the necessary temperature is attained.--

Signed and Sealed this

Seventh Day of October, 1986

[SEAL]

*Attest:*

*Attesting Officer*

DONALD J. QUIGG

*Commissioner of Patents and Trademarks*